(12) United States Patent
Chuang

(10) Patent No.: US 8,093,348 B1
(45) Date of Patent: *Jan. 10, 2012

(54) POLYIMIDES DERIVED FROM NOVEL ASYMMETRIC DIANHYDRIDES

(75) Inventor: Chun-Hua Chuang, Brecksville, OH (US)

(73) Assignee: The United States of America as represented by the Administrator of National Aeronautics and Space Administration, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/894,290

(22) Filed: Aug. 22, 2007

Related U.S. Application Data

(63) Continuation-in-part of application No. 11/890,104, filed on Jul. 19, 2007, now Pat. No. 7,381,849, which is a continuation-in-part of application No. 11/378,553, filed on Mar. 18, 2006, now Pat. No. 7,425,650.

(51) Int. Cl.
*C08G 69/26* (2006.01)
(52) U.S. Cl. .................................. 528/271; 528/332
(58) Field of Classification Search .................. None
See application file for complete search history.

(56) References Cited

U.S. PATENT DOCUMENTS

| | | | | |
|---|---|---|---|---|
| 3,940,426 | A | 2/1976 | Itatani | 528/353 |
| 4,294,976 | A | 10/1981 | Itatani | 560/76 |
| 4,645,821 | A * | 2/1987 | Malinge et al. | 528/331 |
| 4,958,002 | A | 9/1990 | Imatani | 528/353 |
| 5,258,530 | A | 11/1993 | Katsura | 549/241 |
| 2003/0088120 | A1 | 5/2003 | Yamamoto | 560/76 |

FOREIGN PATENT DOCUMENTS

FR  2723099  * 2/1999

OTHER PUBLICATIONS

Database CAS citation 1985:407216 [retrieved Nov. 10, 2009] from STN; Columbus, OH, USA.*
Database CAS citation 1986:553750 [retrieved Nov. 10, 2009] from STN; Columbus, OH, USA.*
Fang et al., Polymer (2003), 44(9), 2641-2646.*
Database CAS citation 2005:1089632 [retrieved Nov. 10, 2009] from STN; Columbus, OH, USA.*
Database CAS citation 1992:72313 [retrieved Nov. 10, 2009] from STN; Columbus, OH, USA.*
Vol. 61, Part 8, pp. o2610-o2612, Aug. 2005, *WestCHEM, Department of Chemistry, University of Glasgow, University Avenue, Glasgow G12 8QQ, Scotland, Correspondence e-mail: d.price@chem.gla.ac.uk, Andrew J. Robertson and Daniel J. Price.

* cited by examiner

*Primary Examiner* — Karl J Puttlitz
(74) *Attorney, Agent, or Firm* — James V. Tura, Esq.; Robert H. Earp, III

(57) ABSTRACT

This invention relates to the compositions and processes for preparing thermoset and thermoplastic polyimides derived from novel asymmetrical dianhydrides: specifically 2,3,3',4' benzophenone dianhydride (a-BTDA), and 3,4'-(hexafluoroisopropylidene)diphthalic anhydride (a-6FDA). The a-BTDA anhydride is prepared by Suzuki coupling with catalysts from a mixed anhydride of 3,4-dimethylbenzoic acid or 2,3-dimethylbenzoic acid with 2,3-dimethylphenylboronic acid or 3,4-dimethylphenylboronic acid respectively, to form 2,3,3',4'-tetramethylbenzophenone which is oxidized to form 2,3,3',4'-benzophenonetetracarboxylic acid followed by cyclodehydration to obtain a-BTDA. The a-6FDA is prepared by nucleophilic triflouoromethylation of 2,3,3',4'-tetramethylbenzophenone with trifluoromethyltrimethylsilane to form 3,4'-(trifluoromethylmethanol)-bis(o-xylene) which is converted to 3,4'-(hexafluoroisopropylidene-bis(o-xylene). The 3,4'-(hexafluoroisopropylidene)-bis(o-xylene) is oxidized to the corresponding tetraacid followed by cyclodehydration to yield a-6FDA.

11 Claims, No Drawings

POLYIMIDES DERIVED FROM NOVEL ASYMMETRIC DIANHYDRIDES

RELATED U.S. APPLICATION

This application is a continuation-in-part of application Ser. No. 11/890,104 filed Jul. 19, 2007 now U.S. Pat. No. 7,381,849, which in turn is a continuation-in-part of application Ser. No. 11/378,553 filed Mar. 18, 2006 now U.S. Pat. No. 7,425,650 B1.

ORIGIN OF INVENTION

The invention described herein was made by an employee of the United States Government and may be manufactured and used by or for the Government for governmental purposes without the payment of any royalties thereon or therefor.

FIELD OF THE INVENTION

This invention relates to the composition and the process for preparing polyimides derived from asymmetric dianhydrides namely; 2,3,3',4'-biphenyldianhydride (a-BPDA), 2,3,3',4'-benzophenone dianhydride (a-BTDA), 3,4'-methylenediphthalic anhydride (a-MDPA) and 3,4'-(hexafluoroisopropylidene)diphthalic anhydride (a-6FDA). These dianhydrides were prepared by cross-coupling dimethylphenylboronic acid and o-xylene derivatives via Suzuki coupling with various catalysts to form 2,3,3',4'-tetramethylbiphenyl and 2,3,3',4'-tetramethylbenzophenone. The asymmetrical tetramethylbiphenyl and the tetramethylbenzophenone were oxidized to the corresponding tetracarboxylic acids which were then converted to asymmetrical 2,3,3',4'-biphenyl dianhydride and 2,3,3',4'-benzophenone dianhydride. In addition, the benzophenone tetracarboxylic acid can be reduced by hydrazine hydrate to 3,4'-methylene diphthalic tetracarboxylic acid which is converted to the corresponding 3,4'-methylenediphthalic anhydride. The unique feature of this invention is that it allows for the production of a series of asymmetric dianhydrides, not only a-BPDA, but also a-BTDA, a-MDPA and a-6FDA. This capability of producing a-BPDA, a-BTDA, a-MDPA and a-6-FDA, will provide innovation for the preparation of high $T_g$, low-melt viscosities and colorless polyimides with interesting and novel properties for aerospace and electronic applications.

More specifically, this invention relates to the composition and process for preparing polyimides derived from intermediates 2,3,3',4' benzophenonetetracarboxylic acid or 3,4'-(hexafluoroisopropylidene) diphthalic acid and the corresponding asymmetric anhydrides. For example, thermosetting polyimides derived from asymmetrical 2,3,3',4'-biphenyl dianhydride (a-BPDA) have been shown to produce low melt viscosity and high $T_g$ polyimides for resin transfer molding; see the Proceedings of the SAMPE Symposium, Long Beach, Calif., May 1-5, 2005. Recently, it was discovered that asymmetric 2,3,3',4'-biphenyl dianhydride (a-BPDA) reacted with diamines and an endcap to produce polyimides with lower-melt viscosities and higher glass transition temperatures. ($T_g$) than the symmetrical 3,3',4,4'-biphenyl dianhydride (s-BPDA); see High Performance Polymers, Vol. 13, 355 (2001), and Vol 15, 375 (2003).

This invention particularly relates to novel compositions and processes for the preparation of polyimides derived from asymmetric dianhydrides, namely, 2,3,3',4'-benzophenone dianhydride (a-BTDA) and 3,4'-(hexafluoroisopropylidene) diphthalic anhydride (a-6FDA). The a-BTDA was prepared by Suzuki coupling with palladium catalysts from 3,4-dimethylphenylboronic acid or 2,3-dimethylphenylboronic acid and a mixed anhydride of 2,3-dimethylbenzoic acid and 3,4-dimethylbenzoic acid to form 2,3,3',4'-tetramethylbenzophenone which was oxidized to form 2,3,3',4'-benzophenonetetracarboxylic acid followed by cyclodehydration to obtain a-BTDA. The a-6FDA tetracid was prepared by nucleophilic trifluoromethylation of 2,3,3',4'-tetramethylbenzophenone with trifluoromethyltrimethylsilane to form 3,4'-(trifluoromethylmethanol)-bis(o-xylene), which is converted to 3,4'-(hexafluoroisopropylidene)-bis(o-xylene). The 3,4'-(hexafluoroisopropylidene)-bis(o-xylene) is oxidized to the corresponding tetraacid followed by cyclodehydration to yield a-6FDA. Thermoplastic and thermoset polyimides and co-polyimides derived from a-BTDA and a-6FDA can be made from a mixture of one or more of these dianhydrides (or the corresponding acid esters or isoimide derivatives) and one or more diamine with or without a monofunctional reactive endcap (such as nadic or phenylethynyl groups) or non-reactive terminating endcap (e.g. phthalic anhydride or aniline) in stoichiometric or non-stoichiometric amounts in solvent or neat without a solvent.

BACKGROUND OF THE INVENTION

Currently, for example, asymmetrical a-BPDA is being prepared from o-xylene via an oxidative coupling reaction which essentially yields a mixture of 3,3',4,4'-biphenyl dianhydride (s-BPDA) and a minor product (2-6%) of a-BPDA. Consequently, a-BPDA is being produced in limited quantity and therefore is not commercially available in sufficient amounts, despite an enormous interest in preparing polyimides using a-BPDA. This disclosure provides alternative and more efficient processes for producing polyimides derived from asymmetric 2,3,3',4'-biphenyl dianhydride (a-BPDA), 2,3,3',4'-benzophenone dianhydride (a-BTDA), 3,4'-methylenediphthalic anhydride (a-MDPA) and 3,4'-(hexafluoroisopropylidene)diphthalic anhydride (a-6FDA).

The prior art (U.S. Pat. No. 3,940,426, UBE Industries) process for making a-BPDA relies on oxidative coupling of o-xylene or o-phthalate with an organic acid salt of palladium under oxygen pressure to produce a mixture of symmetrical and unsymmetrical intermediates which are oxidized and cyclodehydrated to form a mixture of a-BPDA and s-BPDA. This mixture requires the additional process of separating the two isomers.

U.S. Pat. No. 4,294,976 discloses a process for preparing a mixture of biphenyltetracarboxylic acids (3,3',4,4'-isomer, 2,3,3',4'-isomer and 2,2',3,3' isomer) via an oxidative coupling of either o-xylene or o-phthalate in the presence palladium catalyst followed by hydrolysis. The mixture of isomeric biphenyltetracarboxylic acids were then subjected to fractionally recrystallization to obtain the corresponding 2,3,3',4'-(minor amount) and 3,3',4,4'-(major amount) and minute amounts of 2,2',3,3'-biphenyldianhydrides.

U.S. Pat. No. 4,958,002 discloses a dehydration process to obtain 3,3',4,4'-biphenyl dianhydride after the corresponding 3,3',4,4'-biphenyltetracarboxylic acid was isolated from 2,3, 3',4'-biphenyltetracarboxylic acid. U.S. Pat. No. 5,258,530 (Mitsibishi) describes a coupling reaction of phthalic anhydride to form a mixture of 2,3,3',4'-(major) and 2,3,3',4'-(minor) biphenyl dianhydrides. U.S. Patent Publication No. 0088120 A1 (2003) discloses a process for producing predominately 2,3,3',4'-biphenyl dianhydride (a-BPDA) with a minor amount of 3,3',4,4'-biphenyldianhydride (s-BPDA) using palladium and copper catalyst with bidentate ligand. These prior art processes all yield mixtures of asymmetrical dianhydrides together with symmetrical dianhydrides, which then requires the separation of these isomers. In comparison, this invention discloses asymmetrical coupling of dimethylphenylboronic acid with o-xylene derivatives to provide asymmetrical dianhydrides without contamination by the symmetrical dianhydrides.

SUMMARY OF THE INVENTION

By employing a cross-coupling reaction (Suzuki coupling) with 3,4-dimethyl or 2,3-dimethylphenylboronic acid and 3- or 4-substituted o-xylenes in the presence of catalysts, this invention exclusively produces asymmetric precursors; namely, 2,3,3',4'-tetramethylbiphenyl and 2,3',3',4'-tetramethylbenzophenone. These precursors are subsequently oxidized to produce asymmetric tetracarboxylic acids which are converted to the corresponding dianhydrides.

These asymmetric dianhydrides are useful in preparing polyimides which comprise an important class of polymers because of their desirable characteristics i.e. low dielectric constant, high breakdown voltage, good wear resistance, radiation resistance, inertness to solvents, good adhesion properties, hydrolytic stability, low thermal expansion, long-term stability, and excellent mechanical properties. Specifically, high temperature polyimides, such as PMR-15, are extremely valuable particularly for aerospace applications. However, making components from these polymers via prepreg process is labor intensive and expensive. Resin Transfer Molding (RTM) is a more cost-effective alternative to making aerospace components and has been successfully deployed with lower temperature polymers such as the epoxies and bismaleimides (BMI).

A unique feature of this invention is the processes for preparing novel asymmetrical dianhydrides, namely, a-BTDA and a-6FDA, without the contamination of their symmetrical isomers (s-BTDA and s-6FDA). The a-BTDA and a-6FDA can be used to formulate or prepare polyimides with low-melt viscosities without the use of high-boiling point organic solvents such as N-methyl-pyrrolidine (NMP) whereas the conventional polyimides derived from s-BTDA and s-6FDA usually provide high viscosity products.

Accordingly, it is a primary object of this invention to provide polyimides derived from asymmetric dianhydrides, namely: 2,3,3',4'-benzophenone dianhydride (a-BTDA) and 3,4'-(hexafluoroisopropylidene) diphthalic anhydride (a-6FDA).

It is another object of this invention to provide a process for preparing polyimides derived from 2,3,3',4'-benzophenonetetracarboxylic acid and 3,4'-(hexafluoroisopropylidene) diphthalic acid and the corresponding asymmetric anhydrides (a-BTDA and a-6FDA).

It is another object of this invention to provide novel processes for the preparation of polyimides derived from a-BTDA and a-6FDA, and the compositions derived from said processes.

It is another object of this invention to provide processes for preparing asymmetrical tetracarboxylic acids and the corresponding dianhydrides (a-BTDA and a-6FDA) useful in producing polyimides having lower-melt viscosities and high glass transition temperatures ($T_g$).

It is a further object of this invention to provide processes for the preparation of polyimides derived from the synthesis of a-BTDA and a-6FDA obtained by cross-coupling dimethylphenylboronic acid with substituted o-xylenes to produce asymmetric precursors which are further reacted to form the corresponding tetracarboxylic acids and subsequently converted to the corresponding asymmetric dianhydrides.

These and other objects will become more apparent from a further and more detailed description of the invention.

DETAILED DESCRIPTION OF THE PREFERRED EMBODIMENTS

Polyimides are derived from dianhydrides illustrated in the reactions in Scheme I. The asymmetric dianhydrides are obtained by cross-coupling o-xylene derivatives (I) and (II), if (I) is a 3-boron substituted o-xylene, then (II) is a 4-substituted o-xylene, or if (I) is a 4-boron substituted o-xylene, then (II) is a 3-substituted o-xylene derivative. 2,3,3',4'-biphenyl dianhydride (a-BPDA) is prepared by cross-coupling (I) and (II), where X is selected from the group consisting of F, Cl, Br, I, $OSO_2CF_3$, $OSO_2CH_3$ and Y is $(OH)_2$, or $(OR')_2$, where R' is a lower alkyl group such as $CH_3$, $C_2H_5$, i-Pr, in order to form the asymmetrical 2,3,3',4'-tetramethylbiphenyl (III) in a common organic solvent, e.g. toluene, N,N-dimethylormamide (DMF), dimethoxyethane (DMF), 1,4-dioxane, tetrahydrofuran (THF), anisole, or aqueous solution with or without phase transfer catalysts in the presence of palladium or nickel catalysts, either with or without a co-catalysts or co-ligands, such as Pd $(PPh_3)_4$, $Pd(OAc)_2$, Pd $(PPh_3)_2Cl_2$, $PdCl_2(CH_3CN)_2$, $Pd(dba)_2/P(t-Bu)_2$, $Pd_2(dba)_2/[t-Bu)_2PH]BF_4$, $NiCl_2$ $(PPh_3)_2$, $NiCl_2(PCy_3)_2$, $NiCl_2(dppf)$, $NiCl_2(dppe)$, $NiCl_2$ (dppb), and their corresponding polymer bound palladium or nickel catalysts.

Compound (III) is oxidized by potassium permanganate ($KMnO_4$), chromium trioxide ($CrO_3$), or by other oxidation methods such as low or high pressure nitric acid oxidation, catalytic oxidation, in air or in oxygen to form the 2,3,3',4'-biphenyltetracarboxylic acid (IV), which upon dehydration e.g. by acetic anhydride or thermal dehydration, yields 2,3, 3',4'-biphenyl dianhydride a-BPDA (V). Alternatively, compounds (I) and (II) are cross-coupled with carbon monoxide gas in the presence of the Pd or nickel catalysts to form the asymmetrical 2,3,3',4'-tetramethylbenzophenone (VI), which is further oxidized e.g. by $KMnO_4$, $CrO_3$, nitric acid oxidation, or with other known catalytic oxidation methods in air or oxygen to form 2,3,3',4'-benzophenonetetracarboxylic acid (VII) which is then dehydrated by acetic anhydride or thermally cyclodehydrated to yield 2,3,3',4'-benzophenone dianhydride a-BPDA (VIII). Alternatively, 2,3,3',4'-benzophenonetetracarboxylic acid (VII) is reduced by hydrazine to form 3,4'-methylenediphthalic acid (IX), which upon dehydration e.g. by acetic anhydride yields 3,4'-methylenediphthalic anhydride (X) a-MPDA.

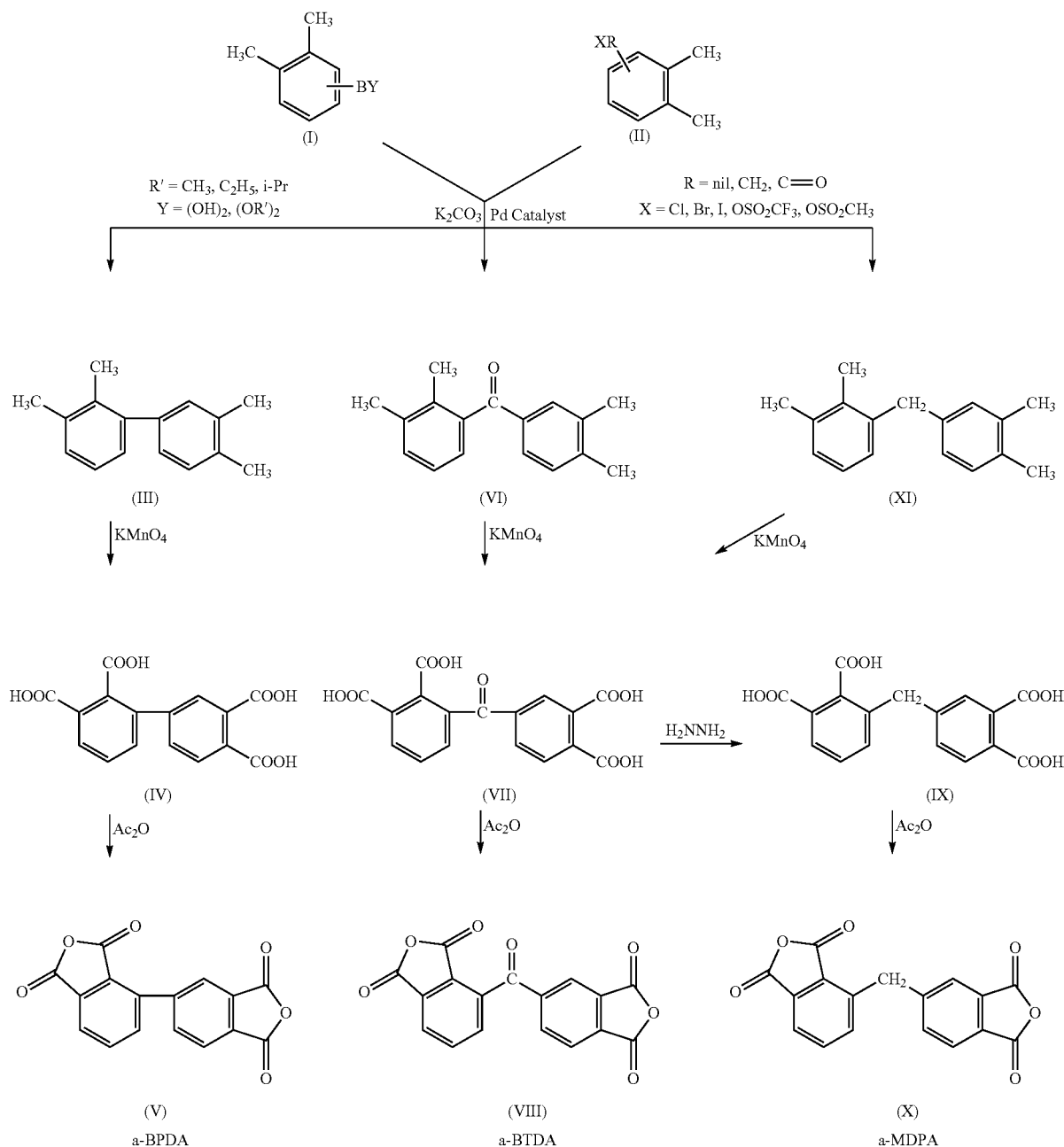

Scheme I Synthesis of Asymmetric Dianhydrides from o-Xylene Derivatives

In Scheme II, a similar Suzuki cross-coupling reaction is carried out between 3- or 4-boron-substituted o-xylene (1), boron-substituted phthalic derivative (1a) or boron-substituted phthalic diester (1b), and 4- or 3-halo-substituted phthalic anhydrides, phthalic ester or phthalimides (2), or diesters of phthalic acid respectively, to produce the coupled asymmetrical 4-(2,3-dimethylphenyl)phthalic anhydride, phthalic ester or phthalimide (3). Compound (3) can be hydrolyzed e.g. by potassium hydroxide, followed by oxidation e.g. by $KMnO_4$, $CrO_3$ and other oxidizing methods such as low or high pressure nitric acid or with catalytic oxidation in air or oxygen to afford 2,3,3',4'-biphenyl tetracarboxylic acid (5), which upon dehydration e.g. with acetic anhydride or thermal cyclodehydration to yield 2,3,3',4'-biphenyl dianhydride (a-BPDA). In the presence of carbon monoxide gas, 2,3,3',4'-benzophenone dianhydride (10), (a-BTDA) is produced by similar routes from compounds (1) and (2) via compounds (7), (8) and (9) as shown in this reaction.

Alternatively, 2,3,3',4'-benzophenonetetracarboxylic acid (9) is obtained through $KMnO_4$ oxidation of (2,3-dimethylphenyl)-α-methylphthalic acid (12) after hydrolysis or from the corresponding phthalimide (11) via the Suzuki coupling of an o-xylene derivative (1) with α-halomethylphthalic anhydride or α-halomethylphthalimide (2) with palladium or nickel catalysts. 2,3,3',4'-benzophenone tetracarboxylic acid (9) can be reduced by hydrazine to 3,4'-methylene diphthalic acid Scheme II Synthesis of Asymmetrical Dianhydride between o-Xylene Derivative and Phthalic Anhydride or Phthalimide Derivatives

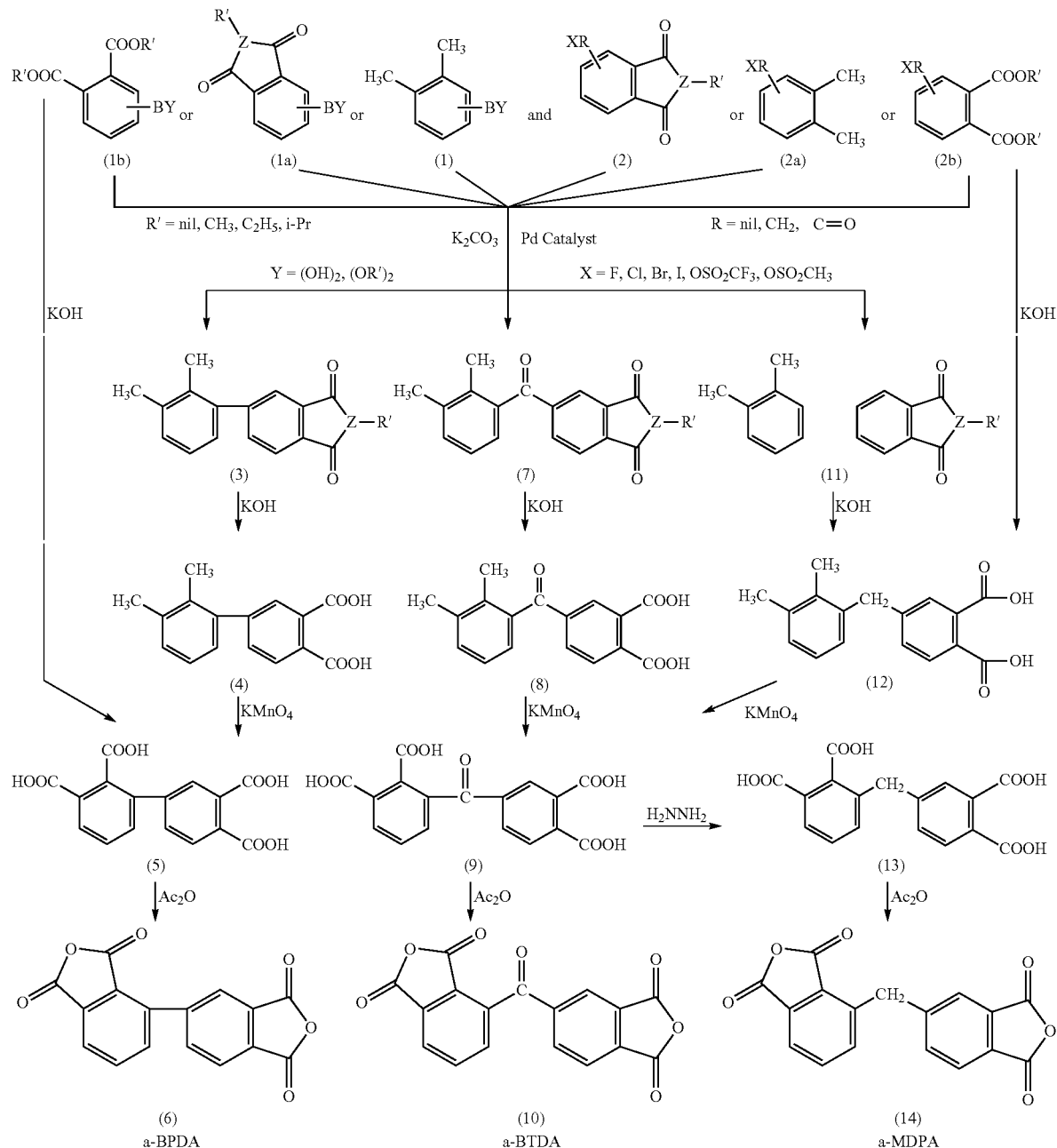

(13), which upon dehydration yields 3,4'-methylene diphthalic anhydride (14) (a-MDPA). In the cross-coupling reactions, X is selected from the group consisting of a halogen e.g. Cl, F, Br, I, or $OSO_2CF_3$ and $OSO_2CH_3$. Y is either $(OH)_2$, or $(OR')_2$. Z is either oxygen or nitrogen. R is —$CH_2$, —C=O, or nil. R' is a lower alkyl such as $CH_3$, or $C_2H_5$, and B is boron.

The dianhydrides prepared by these processes are particularly useful in preparing polyimides from one or more of a combination of reactants comprising dianhydrides selected from the group consisting of 2,3,3',4'-biphenyldianhydride (a-BPDA), 2,3,3',4'-benzophenone dianhydride (a-BTDA), and 3,4'-methylenediphthalic anhydride (a-MDPA), with at least one multifunctional amine such as diamines and an endcap that can be melt-processed at temperatures between 232-270° C. (450-520° F.), without any solvent. The imide oligomers of this reaction have low-melt viscosities of 1-60 poise at 260-280° C. These imide oligomers are amenable to TRM, VARTM or resin infusion processes at 260-280° C. to product high quality polymer composites comprising carbon, glass, quartz or synthetic fibers for use at temperatures ranging up to about 550° to 650° F.

The preferred polyimides of this invention are derived from anhydrides specifically illustrated in Schemes III and IV, which provides novel processes for preparing asymmetrical 2,3,3',4'-benzophenone dianhydride (a-BTDA) and asymmetrical 3,4'-(hexafluoroisopropylidene)diphthalic anhydride (a-6FDA) without the complicated process of separating isomers. The 2,3,3',4'-benzophenone dianhdride (a-BTDA) is prepared by employing the cross-coupling of specific pair of dimethylphenylboronic acid with a mixed anhydride of dimethylbenzoic acid, generated in situ or prepared externally, to obtain the intermediate 2,3,3',4'-tetramethylbenzophenone (4). The mixed dianhydride can be prepared by reacting 3,4-dimethylbenzoic acid or 2,3-dimethylbenzoic acid with either a dialkyl dicarbonate, alkyl chloroformate, alkyl acid halides (acid chloride preferred) or alkyl dianhydrides where the alkyl groups includes primary, secondary and tertiary alkyl groups of $C_1$-$C_6$. The catalysts for the cross-coupling reaction includes, but is not limited to $Pd(PPh_3)_4$, $Pd(PPh_3)_2Cl_2$, $Pd(PCy_3)_2$, $Pd(OAc)_2$, $PdCl_2$ $(CH_3CN)$, and $Pd(dba)_2/p(t-Bu)_2$. The co-catalysts or co-ligands include but not limited to $PPh_3$, $PCy_3$, $P(p-MeOC_6H_5)_3$, $P(o-Tol)_3$, and 1,1'-bis(diphenylphosphino) ferrocene (DPPF). Other additives used in the cross-coupling reaction can include water, NaI, NaF, $Na_2CO_3$, KI, KF, $K_2CO_3$, $K_3PO_4$ and N,N' dicyclohexylcarbodiimide (DCC).

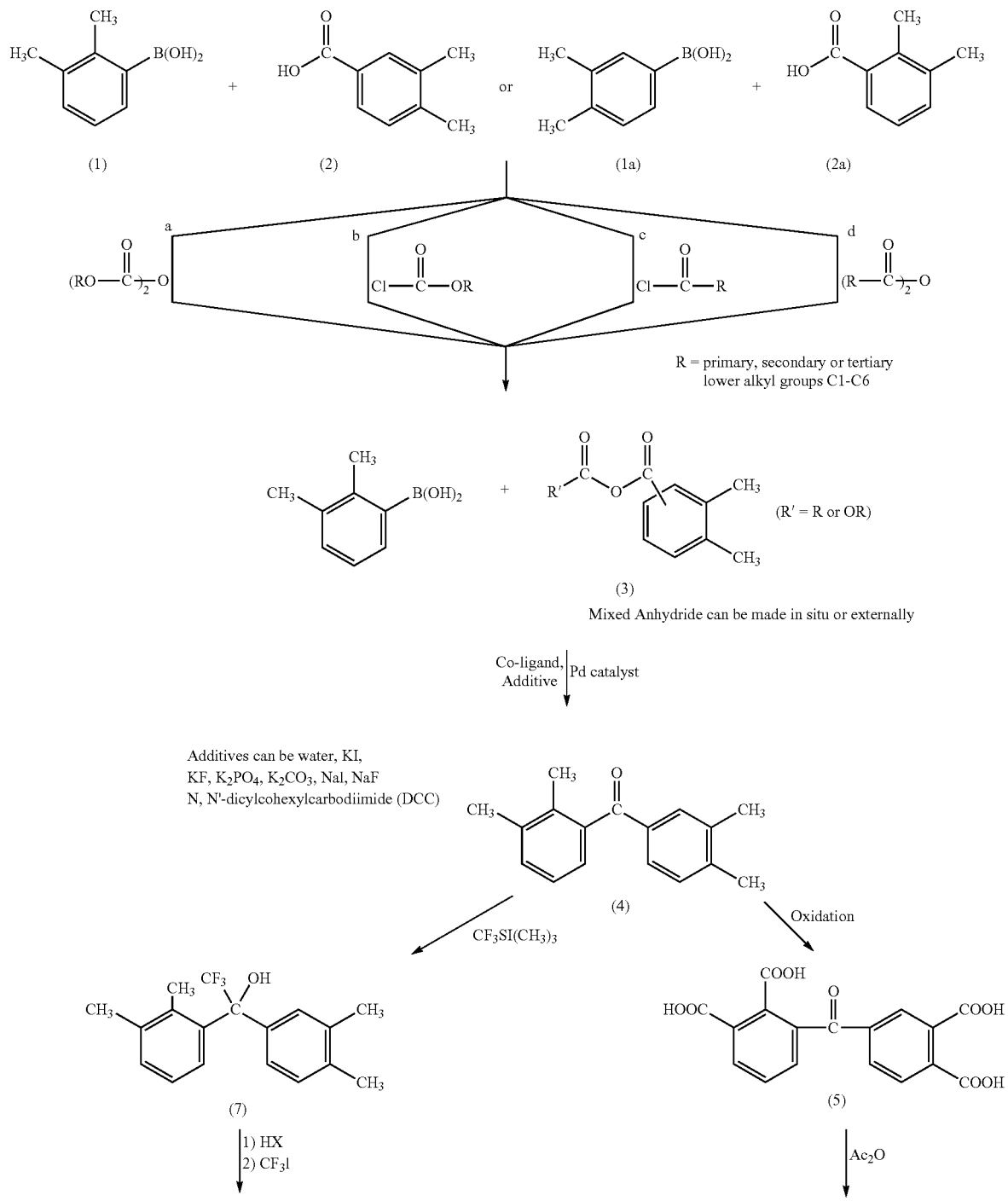

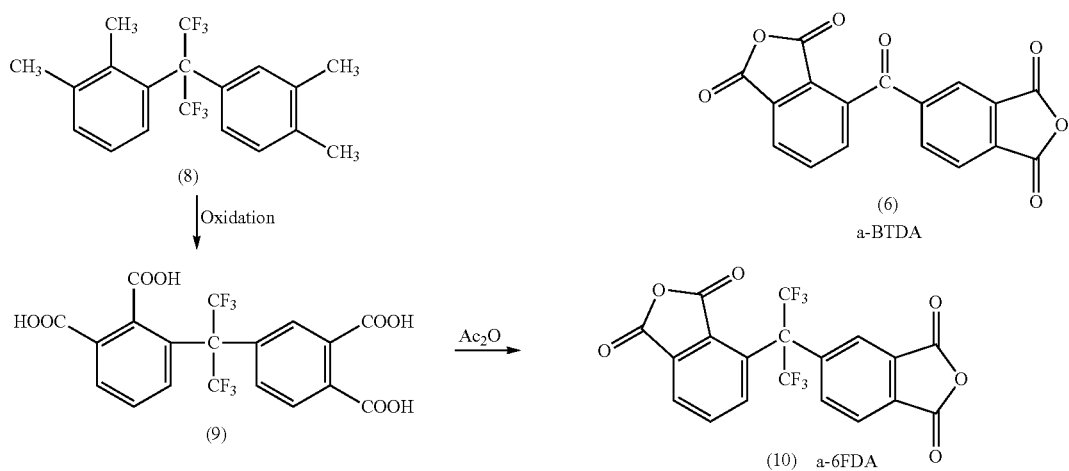
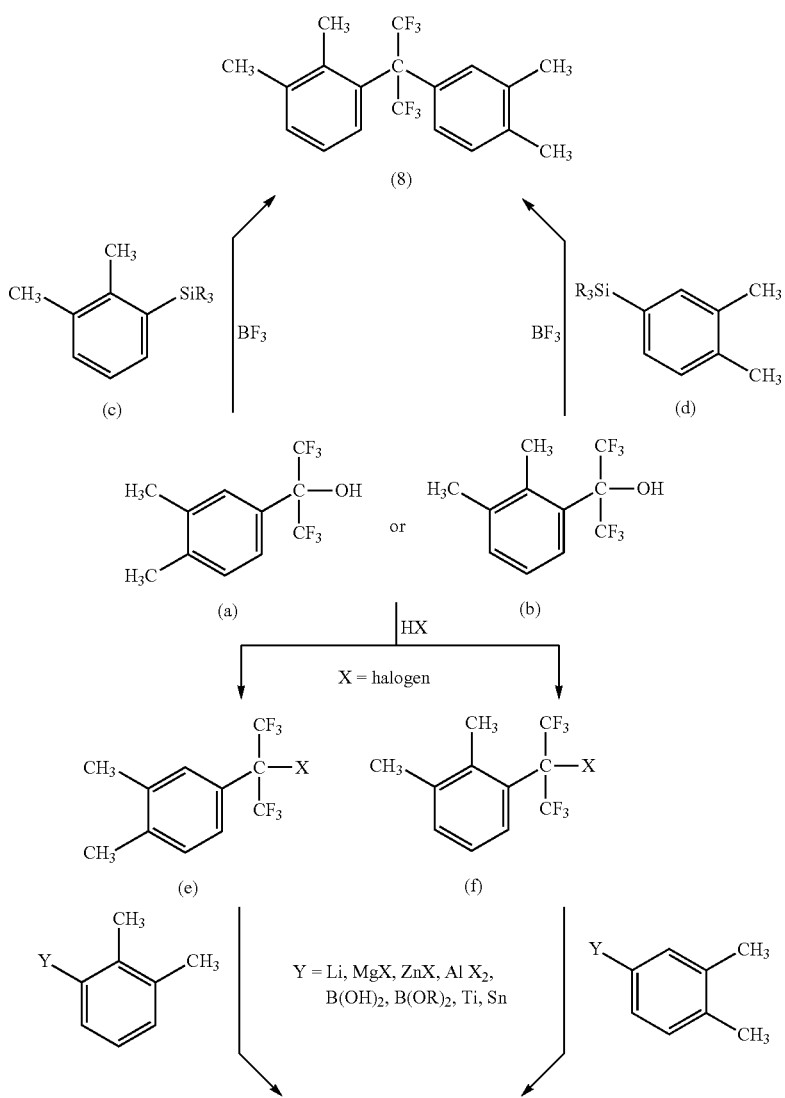
Scheme IV ALternative Synthesis of a-6FDA

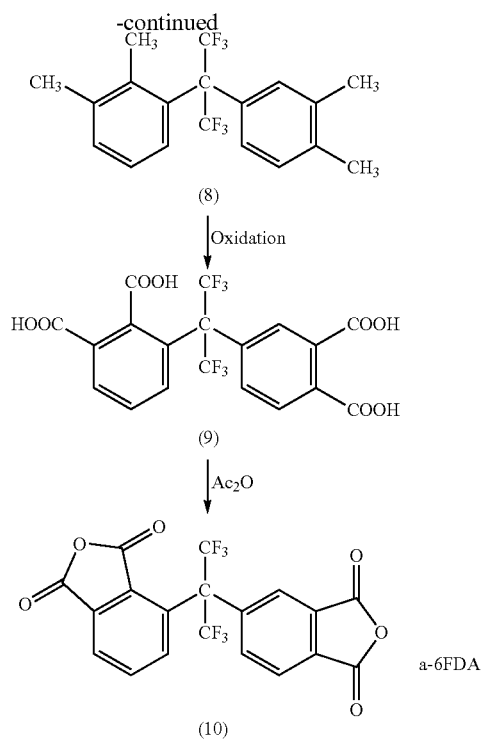

The 2,3,3',4'-tetramethylbenzophenone is reacted with trifluoromethyltetramethylsilane $CF_3Si(CH_3)_3$ and further converted to 3,4'-(hexafluoroisopropylidene)bis-o-xylene (8). Alternatively, 3,4'-(hexafluoroisopropylidene)bis-o-xylene (8) is also prepared from two different routes as shown in Scheme IV. A) Via the coupling of either 2-(3,4-dimethylphenyl)-hexafluoro-2-propanol (a) or 2-(2,3-dimethylphenyl)-hexafluoro-2-propanol (b) with respective trialkylsilane derivatives of o-xylene (c) and (d). B) By converting (a) and (b) to their corresponding halides (e) and (f) and then coupled with 3- or 4-substituted o-xylene.

The 2,3,3',4'-tetramethylbenzophenone (4) and 3,4'-(hexafluoroisopropylidene)bis-o-xylene (8) are oxidized by potassium permanganate $(KMnO)_4$, chromium trioxide $(CrO_3)$, or by other oxidation methods, such as nitric acid oxidation, or catalytic oxidation in air or oxygen in the presence of catalysts to obtain the corresponding 2,3,3',4'-benzophenone tetracarboxylic acid (5) and 3,4'-(hexafluoroisopropylidene)diphthalic acid (9), respectively. The tetracarboxylic acids (5) and (9) are subsequently reacted with either acetic anhydride or propionic dianhydride, or thermally cyclodehydated to obtain the corresponding 2,3,3',4'-benzophenone dianhydride (a-BTDA) or 3,4'-(hexafluoroisopropylidene)diphthalic anhydride (a-6FDA).

The preparation of asymmetrical BTDA and a-6FDA presents a successful and economical synthesis of asymmetrical 2,3,3',4'-benzophenone dianhydride (a-BTDA) that can be formulated into low-melt viscosity polyimide resins (10-30 poise) that are amenable to low-cost resin transfer molding (RTM) process. Because a-BTDA is an isomer of s-BTDA used in PMR-15, essentially, this invention will afford an RTMable PMR-15 without health hazards associated with PMR-15 composites manufacturing. Additionally, the intermediate 2,3,3',4'-tetramethylbenzophenone also can be used to make asymmetrical 6F-dianhydride. This process can produce asymmetrical 6F-dianhydride (a-6FDA) to yield low viscosity 6F-polyimide resins adaptable to RTM process with potential 30% savings in manufacturing cost. Since this invention can produce novel a-BTDA and a-6FDA exclusively, it's essentially capable of producing a new class of thermoplastic and thermoset polyimides that have the potential of making colorless polyimides for optical and electronic applications.

The thermoplastic polyimides of this invention are prepared from dianhydrides or the ester-acid derivatives thereof selected from the group consisting essentially of:

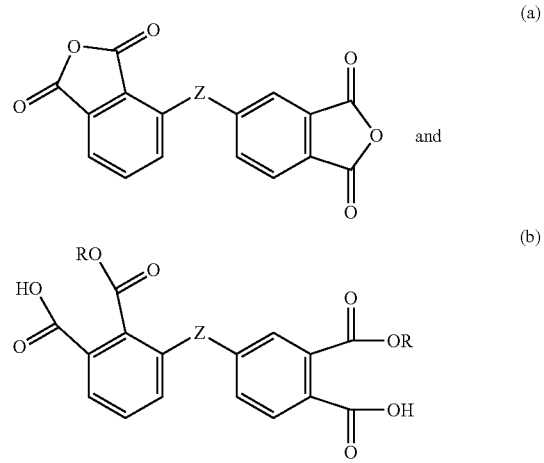

with at least one multifunctional amine, e.g. diamines, in the equivalent stoichiometric ratio or an excess of either the dianhydride or the amine in solvents, such as N-methyl-2-pyrrolidinone (NMP) to form polyamic-acid intermediate, which are then cylcodehydrated at temperatures between 120-200° C. to thermoplastic polyimides having the formula:

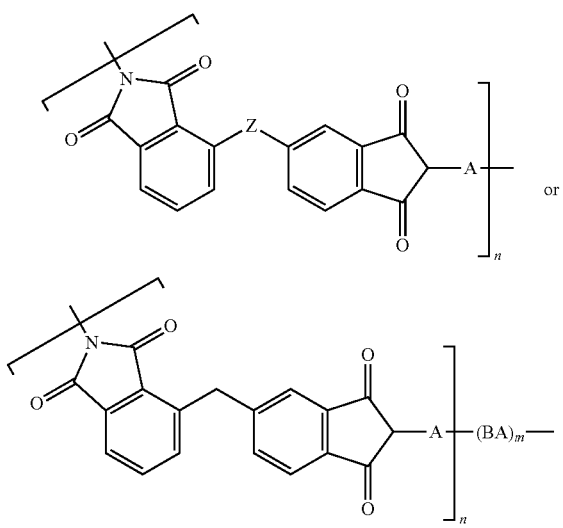

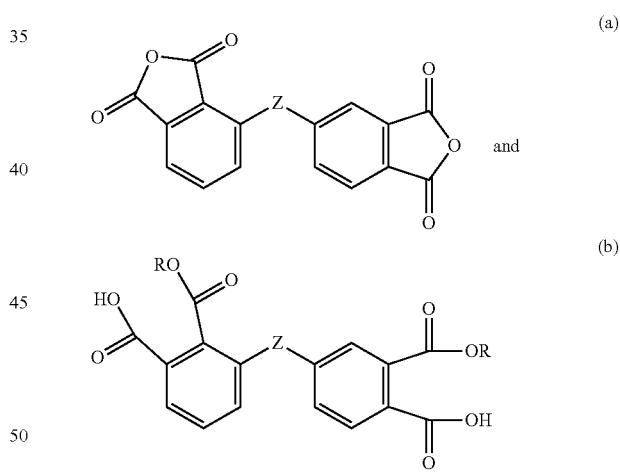

wherein $R_5$ and $R_6$ are alkyl groups of 1-6 carbons, and R" is an alkyl, alkoxy, halogen, $CF_3$, phenyl or phenoxy radical.

The preferred multifunctional amines are the diamines including: meta-phenylenediamine, para-phenylenediamine, 2,2-bis(4-aminophenyl) hexafluoropropane, 2,2-bis(4-aminophenyl)propane, 4,4'-oxydianiline, 3,4'-oxydianiline, 4,4'-methylene dianiline, 3,4'-methylenedianile, 3,3'-methylenedianiline, 4,4'-diaminobenzophenone, 3,4'-diaminobenzophenone, 3,3'-diaminobenzophenone, benzidine, 2,2'-dimethylbenzidine, 2,2'-bis(trifluoromethyl) benzidine, 1,4-bis(4-aminophenoxy)benzene, 1,3-bis(4-aminophenoxy)benzene, 1,3-bis(3-aminophenoxy)benzene, 4,4'-diaminophenylsulfone, 3,4'-diaminosulfone, 4,4'-[1,3-phenylene-bis(1-methylethylidene)], 3,3'-diaminosulfone, 4,4'-[1,4-phenylene-bis(1-methylethylidene)], 3,3'-diaminosulfone, 4,4'-bis(4-aminophenoxy)-biphenyl, 2,2-bis[4-(aminophenoxy)phenyl]propane, and mixtures thereof.

The polyimides terminated with reactive or non-reactive endcaps are prepared from at least one dianhydride and its acid-ester derivatives selected from the group consisting of:

wherein Z is $(CF_3)_2C$, C=O, R is a lower alkyl of 1-6 carbons, B is a dianhydride or its acid-ester derivative other than the dianhydrides (a) or (b) as shown in the above formulas, $(BA)_m$ is the product of B and A, n is equal to 1-100, m is equal to 0-100, and when m=0, it is a homopolymer, and when m is greater than 0, it is a copolymer.

In the above formulas, A is a diamine containing an organic divalent'radical consisting of aliphatic, cycloaliphatic, heterocyclic, siloxane, or aromatic groups linked through bridging atoms or groups. The preferred structure of A is selected from the group consisting essentially of

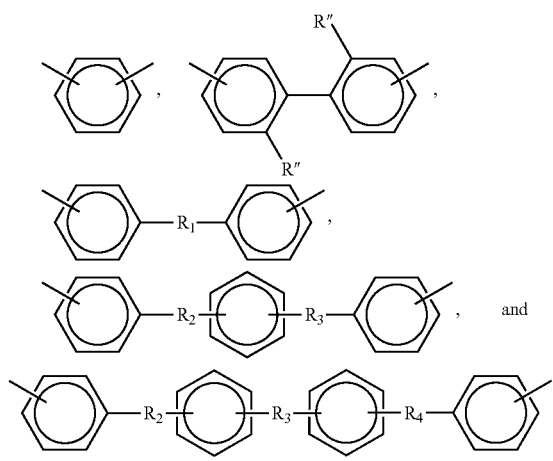

wherein $R_1$, $R_2$, $R_3$, $R_4$ are selected from the group consisting essentially of reacted with at least one multifunctional amine e.g. diamine, $H_2N$-A-$NH_2$, in an equivalent stoichiometric ratio or off-set stiochometry, and with a reactive or non-reactive terminal endcap having a preferred but not limited to a formula selected from the group consisting of

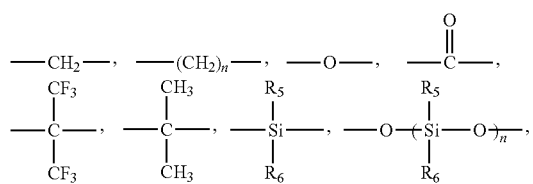

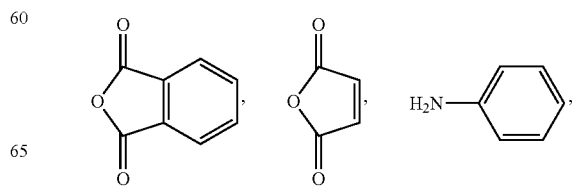

-continued

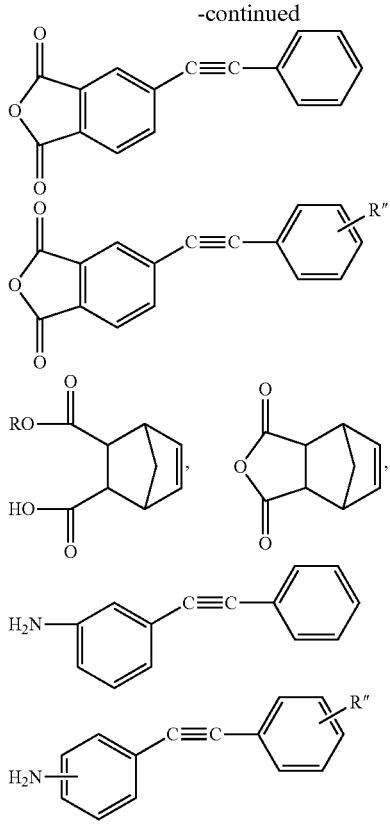

with solvents, such as N-methyl-2-pyrrolidinone or an alcohol such as methanol or ethanol, or without a solvent at high temperature in the melt, to form polyimide oligomers having the formula:

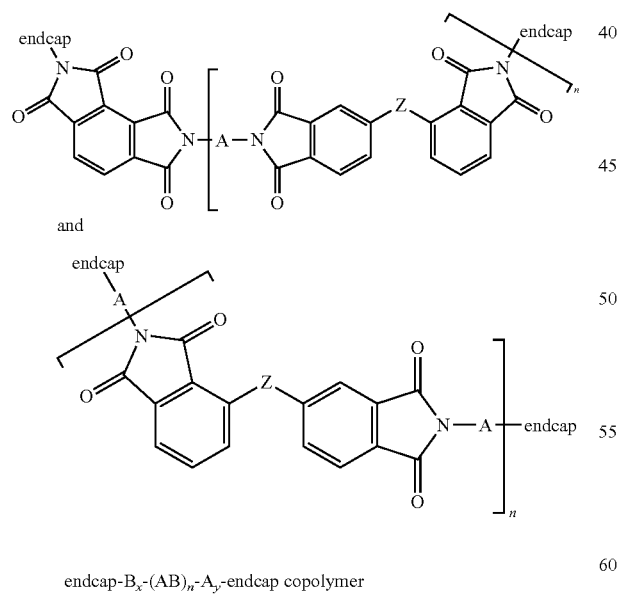

endcap-$B_x$-$(AB)_n$-$A_y$-endcap copolymer wherein Z is $(CF_3)_2C$ or C=O, R is a lower alkyl of $C_1$-$C_6$ carbons, $R''$ alkyl, alkoxy, halogen, $CF_3$, substituted or unsubstituted phenyl or phenoxy radical. B is a dianhydride or its acid-ester derivative selected from either of the above formulas (a) or (b) together with one other dianhydride or its ester-acid derivative, $(AB)_n$ is the product of A and B, n is equal to 1-100, x is equal to 0 or 1.0 and y is equal to 0 or 1.0. However, when x is 0 then y is 1, and when x is 1 then y should be 0.

In the preferred formulas, A is a diamine containing an organic divalent radical consisting of aliphatic, cycloaliphatic, heterocyclic, siloxane, or aromatic groups linked through bridging atoms or groups. The preferred structure of A includes the following:

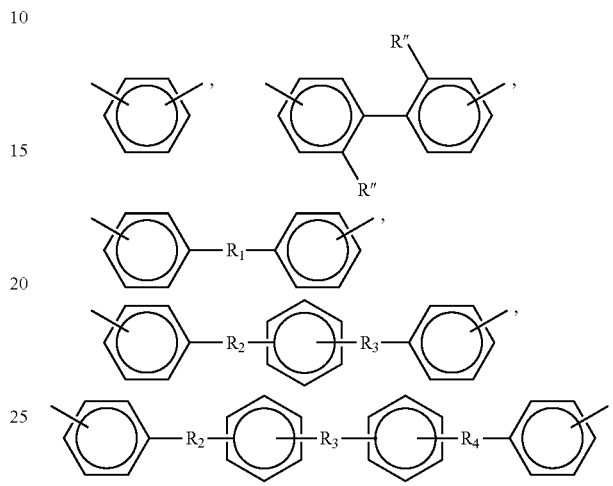

wherein $R_1$, $R_2$, $R_3$, $R_4$ are selected from the group consisting of:

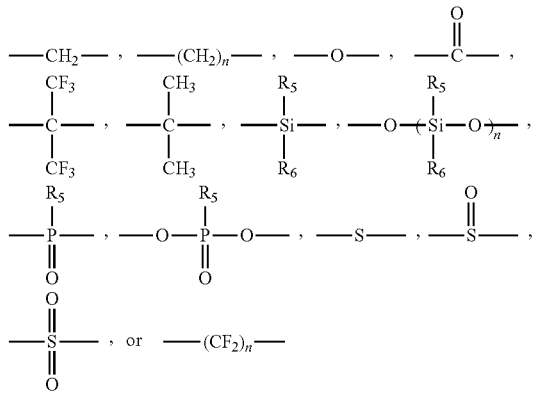

wherein $R_5$ and $R_6$ are alkyl groups.

EXAMPLE 1

Synthesis of 2,3,3',4'-tetramethylbenzophenone (4)

To a 250 ml 3-necked round-bottom flask, 2,3-dimethylphenylboronic acid (3.6 g, 24 mmol), 3,4-dimethylbenzoic acid (3.0 g, 20 mmol), a selected palladium catalyst (0.6 mmol), dimethyl dicarbonate (2.7 g, 30 mmol) and potassium carbonate (6.22 g, 45 mmol) were mixed with 150 ml of dry dioxane. The reaction mixture was heated at 80° C. overnight to become a viscous reaction mixture. 20 ml of water was added to dissolve the heterogeneous reaction mixture, and dioxane was evaporated to dryness. The aqueous solution as extracted with 20 ml of ethyl acetate, dried over anhydrous magnesium sulfate and then evaporated to dryness. The crude product was purified by silica gel column chromatography eluted by hexane/ethyl acetate=20/80 to afford 2.0 g (33%) of the product.

Synthesis of 2,3,3',4'-benzophenonetetracraboxylic acid (5)

2,3,3',4'-tetramethylbenzophenone (2.0 g, 8.4 mmol) and potassium permanganate (5.3 g, 33.6 mmol) were mixed in 25 ml of water in a 100 ml round-bottom flask and the reaction mixture turned purple. The reaction mixture as heated at 90° C. overnight. The reaction mixture turned brown, and the brown $MnO_2$ precipitate was filtered and removed. The aqueous solution was evaporated to dryness to afford 2.5 g (90%) of the desired tetraacid.

Synthesis of 2,3,3',4'-benzophenone dianhydride (6)

2,3,3',4'-benzophenonetetracarboxylic acid (4) (3.7 g, 10 mmol) was suspended in minimum amount of acetic anhydride; (3 g, 2.7 ml) and heated to reflux for 4 hours. The reaction mixture was cooled to room temperature. The corresponding dianhydride precipitated out and was collected and washed with ether to remove trace of acetic acid before drying under vacuum to afford 2.9 g (90%) of a-BTDA.

Synthesis of Thermoplastic Polyimides

EXAMPLE 2

A solution of 2,3,3',4'-benzophenone dianhydride (3.22 g 10 mmol) and 2,2-bis(4-aminophenyl)hexafluoropropane (3.34 g, 10 mmol) in 31 g of dry N-methyl-2-pyrrolidinone (NMP) were stirred at room temperature under nitrogen overnight. Then the resulting polyamic acid was imidized by heating at 150° C. for 2 hours. The solution was cooled down and then precipitated into ethanol to afford fibrous polyimide.

EXAMPLE 3

A solution of 3,4'-(hexafluoroisopropylidene)diphthalic anhydride (4.44 g, 10 mmol) and p-phenylenediamine (1.08 g 10 mmol) in 50 g of dry N-methyl-2-pyrrolidinone (NMP) were stirred at room temperature under nitrogen overnight. Then the resulting polyamic acid solution was imidized by heating at 150° C. for 2 hours. The solution was cooled down and then precipitated into ethanol to afford fibrous polyimide.

EXAMPLE 4

To a solution of 3,4'-(hexafluoroisopropylidene)diphthalic anhydride (4.44 g. 10 mmol) and 2,2'-bis(trifluoromethyl) benzidine (3.2 g. 10 mmol) in 43.3 g of m-cresol, 5 drops of isoquinoline was added. The reaction mixture was heated to reflux under nitrogen to afford a very viscous solution. The solution can be poured into ethanol solution to afford polyimide fibers or can be spun into high strength, high modulus polyimide fibers.

Synthesis of Thermoset Polyimide and Composites

EXAMPLE 5

A solution of 2,3,3',4'-benzophenone dianhydride (12.88 g) and 4-phenylethynylphthalic anhydride (9.92 g) in 26.64 g of methanol were heated to reflux for 1 hour to convert them into the corresponding diester diacid, and then 3,4'-methyl-enedianiline (11.76 g) in 10 g of methanol was added. The solution was concentrated to dryness in a hot plate and then staged at ° C. for 1 hour to afford a polyimide powder.

EXAMPLE 6

A solution of 2,3,3',4'-benzophenone dianhydride (22.17 g) and nacid anhydride anhydride (10.93 g) in 6.68 g of methanol was heated to reflux for 1 hour to make a 50% solution of the corresponding diester acid. After cooling the solution down to room temperature, 20.37 g of 4,4'-methyl-enedianiline in 20.37 of methanol was mixed with the diester diacid solution with stirring. The resulting 50% monomer solution as painted onto unidirectional carbon fibers or fabrics. The prepregs were allowed to be air-dried. The polyimide prepregs can be staged at 150° C. and then cured at 315° C. for 2 hours to form the polyimide carbon fiber composites.

EXAMPLE 7

A solution of 3,4'-(hexafluoroisopropylidene)diphthalic anhydride (17.99 g) and 4-phenylethynylphthalic anhydride (2.23 g) in 24.32 g of absolute ethanol was heated to reflux for 1 hour to form the corresponding diester diacid. Then p-phenylenediamine (4.86 g) in 4.86 g of ethanol was added at room temperature to form a 50% solution. The resulting 50% monomer solution as painted onto unidirectional carbon fibers or fabrics. The prepregs were allowed to be air-dried. The polyimide prepregs can be stated at 150° C. and then cured at 315° C. for 2 hours to form the polyimide carbon fiber composites.

EXAMPLE 8

A mixture of 3,4'-(hexafluoroisopropylidene)diphthalic anhydride (8.88 g), 4-phenylethynylphthalic anhydride (9.92 g) and 3,4'-oxydianiline (8.0 g) were mixed well and then the reaction mixture was heated in an oven at between 200-280° C. for 1 hour to melt all the monomers into forming a polyimide resin with low-melt viscosity (10-30 poise). The low-melt resins can be injected into carbon fiber perform by resin transfer molding (RTM), vacuum assisted resin transfer molding (VARTM) or resin infusion process to form lightweight carbon fiber composites.

While this invention has been described by a number of specific examples, it is obvious that there are other variation and modification that can be made without departing from the spirit and scope of the invention as set forth in the appended claims.

The invention claimed is:
1. Thermoplastic polyimides derived from asymmetric dianhydrides or the ester-acid derivatives thereof selected from the group comprising of:

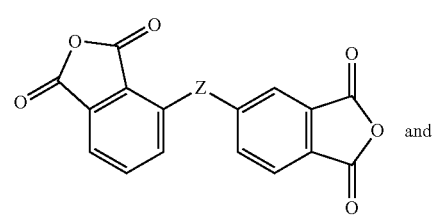

(a)

and

-continued

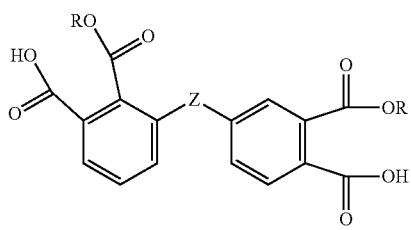
(b)

and approximate stoichiometric amount of at least one multifunctional amine to form thermoplastic polyimides having a formula selected from the group consisting of:

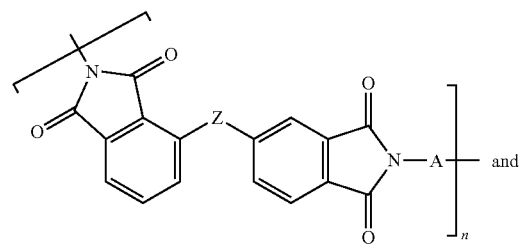
and

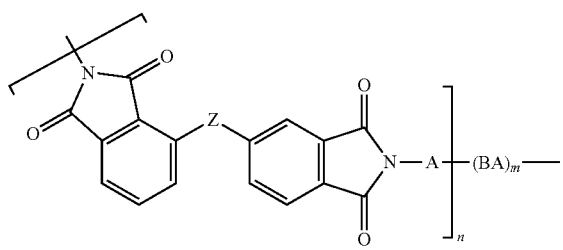

wherein Z is $C(CF_3)_2$, which correspond to the following polyimide structures consisting of:

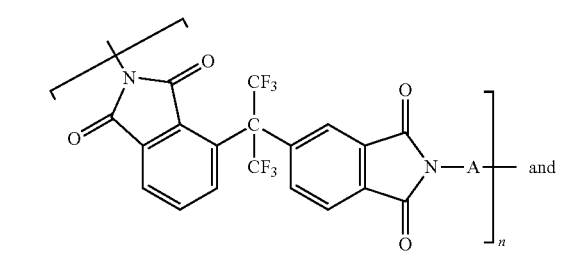
and

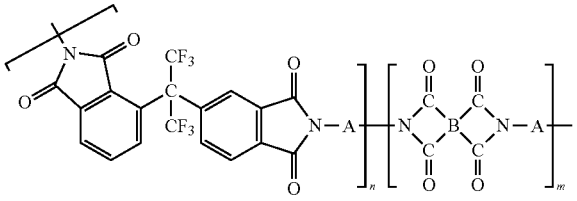

wherein B is a second dianhydride or its ester acid derivative other than (a) and (b), consisting of:

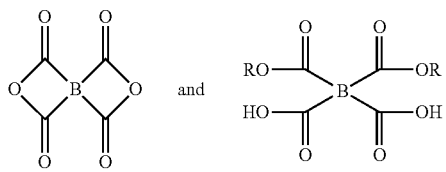
and

R is a lower alkyl radical having 1 to 6 carbon, A is a divalent organic radical of a diamine ($H_2N$-A-$NH_2$), $(BA)_m$ is the reaction product of dianhydride B or its ester acid derivative with a diamine ($H_2N$-A-$NH_2$), n has the value of 1-100, and m has the value of 1-100.

2. The polyimides of claim 1 wherein at least one of the multifunctional amines is a diamine wherein the diamine and dianhydride is in a stoichiometric ratio of 1 to 1.

3. The polyimides of claim 1 wherein at least one of the multifunctional amines is a diamine wherein the diamine or dianhydride is in excess of the stoichiometric ratio.

4. The polyimides of claim 2 wherein the diamine ($H_2N$-A-$NH_2$) contains an organic divalent radical A, consisting of aliphatic, cycloaliphatic, heterocyclic, siloxane, or aromatic groups linked through bridging atoms or groups.

5. Polyimides of claim 4 wherein the structure of divalent radical A is selected from the group consisting of:

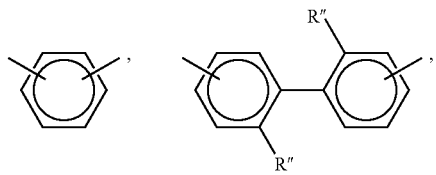

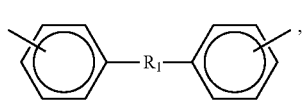

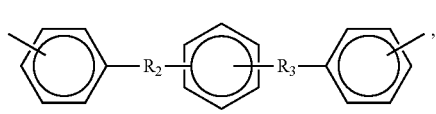

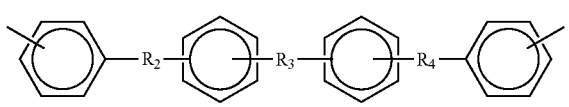

wherein $R_1$, $R_2$, $R_3$, $R_4$ are selected from the group consisting of:

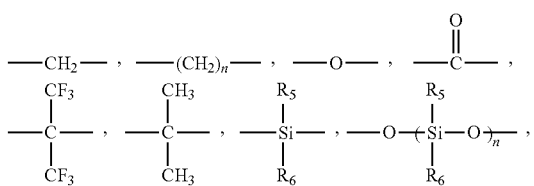

-continued

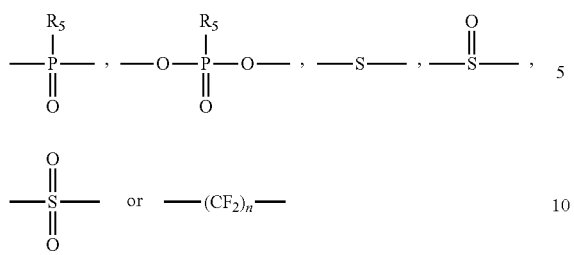

wherein $R_5$ and $R_6$ are alkyl groups, and R" is an alkyl, alkoxy, halogen, $CF_3$, phenyl or phenoxy group.

6. Polyimide derived from asymmetric dianhydrides and the ester-acid derivatives of said dianhydride selected from the group of:

(a)

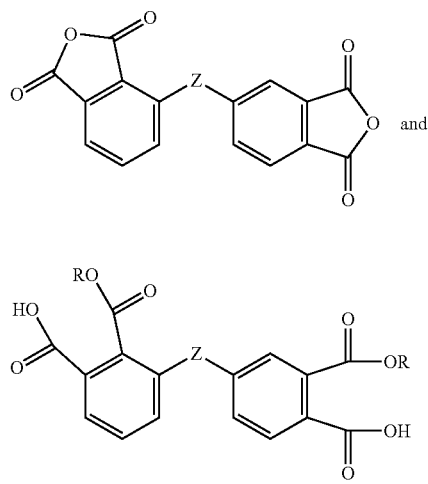

(b)

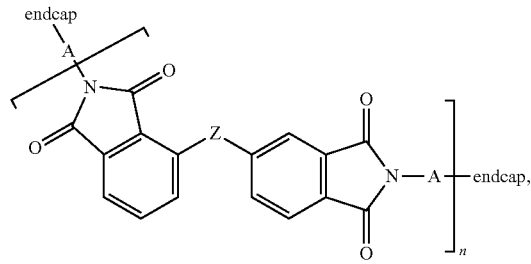

with at least one multifunctional amine, and a terminal endcap to form polyimide having a formula selected from the group consisting of:

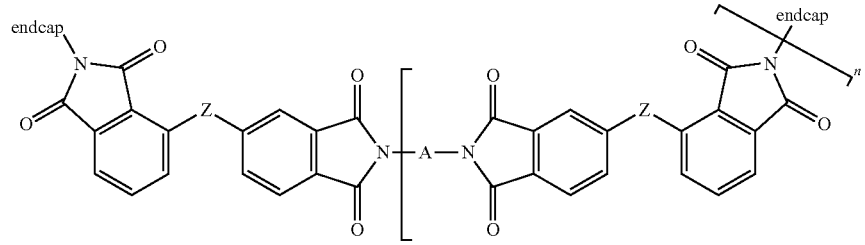

and endcap B'-(AB')$_n$-A$_y$-endcap copolymer wherein A is an organic divalent radical of a diamine [$H_2N$-A-$NH_2$], Z is $C(CF_3)_2$, R is a low alkyl of 1-6 carbon, B' is a dianhydride or the ester-acid derivatives selected from one of the group consisting of:

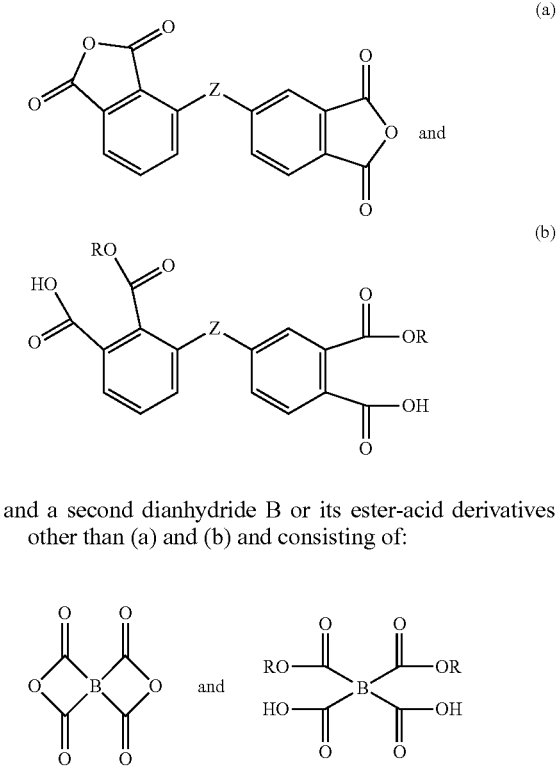

and a second dianhydride B or its ester-acid derivatives other than (a) and (b) and consisting of:

(AB')$_n$ is the reaction product of A and B', n is equal to 1-100, x is equal to zero or one, and y is equal to zero or one.

7. The polyimides of claim 5 wherein the terminal monofunctional endcap is selected from the group consisting of:

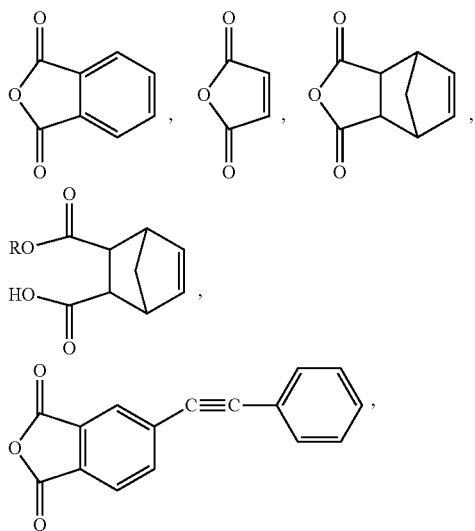

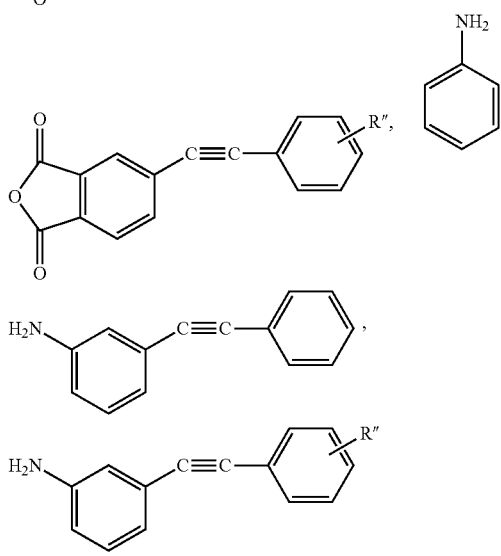

where R is low alkyl of 1-6 carbon, and R" is an alkyl, alkoxy, halogen.

8. The polyimides of claim 6 wherein the diamine ($H_2N$-A-$NH_2$) contains an organic divalent radical Z, consisting of aliphatic, cycloaliphatic, heterocyclic, siloxane, or aromatic groups linked through bridging atoms or groups.

9. Polyimides of claim 8 wherein the structure of divalent radical A is selected from the group consisting of:

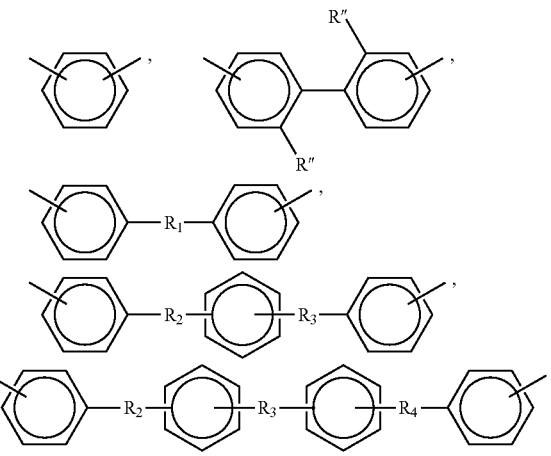

wherein $R_1$, $R_2$, $R_3$, $R_4$ are selected from the group consisting of:

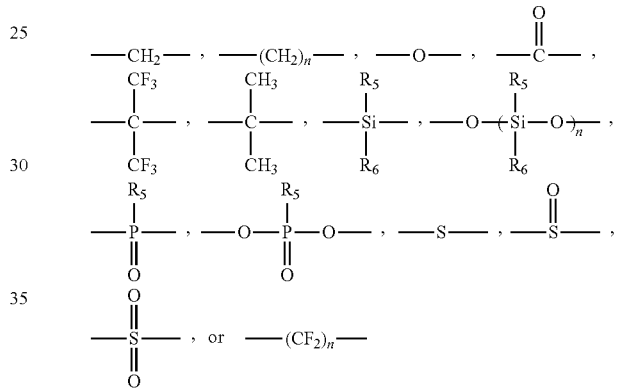

wherein $R_5$ and $R_6$ are alkyl groups, and R" is an alkyl, alkoxy, halogen, $CF_3$, phenyl or phenoxy group.

10. The polyimide of claim 7 wherein at least one the multifunctional amines is a diamine, and either the diamine or dianhydride is in excess of the stoichiometric ratio.

11. The polyimides of claim 6 wherein the polymer is a copolymer having the formula:

endcap-B'$_x$-(AB')$_n$-A$_y$-endcap copolymer wherein when x is zero, y is one; and when x is one y is zero.

\* \* \* \* \*